United States Patent [19]

Morrison

[11] Patent Number: 4,909,783

[45] Date of Patent: Mar. 20, 1990

[54] INTRA-OCULAR PRESSURE APPARATUS

[76] Inventor: David P. Morrison, 875 N. Easton Rd., Doylestown, Pa. 18901

[21] Appl. No.: 110,098

[22] Filed: Oct. 14, 1987

Related U.S. Application Data

[63] Continuation of Ser. No. 886,733, Jul. 16, 1986, abandoned.

[51] Int. Cl.⁴ ............................................. A61M 1/00
[52] U.S. Cl. ..................................... 604/30; 604/121; 604/155; 604/246
[58] Field of Search ............................... 604/7, 27–30, 604/35, 118, 119, 121, 246, 4, 5, 22, 33, 141, 143, 155, 236; 417/491

[56] References Cited

U.S. PATENT DOCUMENTS

| | | | |
|---|---|---|---|
| 2,625,933 | 1/1953 | Salisbury | 604/7 |
| 2,742,901 | 4/1956 | Krauthamer | 604/154 |
| 3,491,749 | 1/1970 | Gidlund | 604/143 |
| 3,572,319 | 3/1971 | Bittner et al. | 604/118 |
| 3,727,614 | 4/1973 | Kniazuk | 604/144 |
| 4,457,747 | 7/1984 | Tu | 604/7 |
| 4,650,461 | 3/1987 | Woods | 604/30 |

Primary Examiner—Stephen C. Pellegrino
Assistant Examiner—Adam J. Cermak
Attorney, Agent, or Firm—Steele, Gould & Fried

[57] ABSTRACT

An apparatus for maintaining intra-ocular pressure while simultaneously removing and replacing fluid in a patient's eye, for example, during cataract surgery, includes a pair of cooperating expansible bodies connected via fluid conduits to the eye. The expansible bodies may be piston/cylinder assemblies such as syringes. The plungers and/or the barrels of the syringes are mechanically linked together for equal and opposite operation of the two syringes, whereby input and output flow are precisely equal. The syringes are preferably placed back to back along a common axis. The barrels are rigidly spaced and a drive means is applied between the spaced barrels and the endwise-connected plungers.

12 Claims, 2 Drawing Sheets

INTRA-OCULAR PRESSURE APPARATUS

This is a continuation of application No. 886,733, filed July 16, 1986 now abandoned.

BACKGROUND OF THE INVENTION

1. Field of the Invention

This invention relates to an aspiration/infusion apparatus for body cavities, and in particular to a precision apparatus adapted for maintaining the pressure within an eye cavity during simultaneous removal and replacement of fluid therein, for example, during opthalmic surgery for removal of cataracts.

2. Description of the Prior Art

A variety of devices are known in the art for control of intra-ocular pressure. Such devices are sometimes combined with hand-held tools adapted for removal and aspiration of intra-ocular material or infusion of fluid to replace the aspirated material. The need to precisely control pressure is known, but in general, the currently available devices are complicated and expensive.

Surgical procedures for removal of cataracts now conventionally involve surgery on a normally pressurized eye. Instruments are passed through small incisions at the edges of the cornea in order to access and remove opaque cataract material clouding the lens, located immediately behind the anterior aqueous chamber of the eye. Cataracts in the lens are broken up by cutting apparatus or vibratory apparatus, and the broken-up material is aspirated together with a quantity of the aqueous fluid in the chamber. In order to maintain normal pressure within the eye, the aqueous fluid is simultaneously replaced by means of a gravity-powered infusion of a balanced salt solution supplied through a needle inserted in the anterior chamber or through a passage in the incision or aspiration instrument. Accordingly, the conventional means of pressure regulation during endophthalmic surgery is to ignore the extent of fluid flow and any variations thereof, and to employ a pressure regulation technique only. In other words, an indefinite quantity of fluid is supplied so long as intra-ocular pressure is less than a predetermined reference pressure.

A cutting apparatus having a co-axial passage for aspiration or infusion is shown in U.S. Pat. No. 4,314,560-Helfgott, et al. A handpiece is disclosed in that patent for conducting operations in the aqueous, vitreous or other intra-ocular tissues. Although both aspiration and infusion are discussed, it appears that these procedures are to be undertaken consecutively rather than concurrently. Pressure is controlled by physical elevation of a column of saline solution connected by a conduit to the intra-ocular chamber being treated.

In U.S. Pat. No. 4,184,491-McGannon and No. 4,157,718-Baehr, two hypodermic needles are inserted into the anterior aqueous chamber of the eye, one of the needles being connected to a pressure regulation device comprising an elevated column of saline solution, and the other being connected to an open tube, providing an unobstructed bleed-off pathway or drain pathway for aspirated fluid. The bleed-off pathway presumably relieves excess pressure which may develop, without the possibility of a reverse flow of fluid toward the supply of saline solution. On the other hand, the unterminated bleed pathway means that a steady current of fluid must be supplied through the pressure regulating device, the fluid flowing through the aqueous chamber of the eye and being bled away, just to maintain pressure. Without regard to whether or not cataract material is removed, the technique requires a flow of fluid through the eye.

U.S. Pat. No. 3,902,495-Weiss, et al., teaches a combined infusion and aspiration device in which an ultrasonic vibration is employed to emulsify cataract tissue. A constant flow pump withdraws emulsified lens tissue and fluid, and an elevated column supplies the fluid. As in McGannon and Baehr, the control seeks to maintain constant pressure at the input. Accordingly, the device not only incidentally causes a steady-state current through the eye, but in fact powers such a flow. According to prior art methods such as those of McGannon, Baehr and Weiss, a relatively large quantity of fluid is forced to wash through the anterior aqueous chamber. During the course of even a brief operation, completing thirty changes of the approximately one cc of fluid present in the anterior aqueous chamber is not uncommon. Special solutions which comprise balanced salt ingredients are available to most nearly satisfy the natural requirements of the eye; however, it is preferable to minimize flow of such foreign fluid, particularly flow using a powered means which is prone to malfunction, causing unnatural over-inflation or under-inflation of the eye.

In U.S. Pat. No. 3,812,855-Banko, a variety of pressure and suction configurations are selectable by the user in order to meet the requirements of a particular surgical procedure. Both a pressure source and a suction source are selectably valved by means of an electrical control mechanism. The availability of a pressure source as well as a suction source, including various sensing and controlling mechanisms, provides the machinery necessary to normalize any detected over-pressure or under-pressure situations. Such over-pressure and under-pressure problems, however, are likely to be caused by the use of powered sources and drains in the first place. The separation of the source and drain powering mechanisms presents a possibility that unwanted or dangerous pressure differentials could be produced, for example upon failure or obstruction of the source or drain. A very dependable system in which the user is relatively assured that over-pressure or under-pressure conditions could not occur is highly preferable over the most sophisticated arrangements in which a variety of malfunction-prone sensors, conduits and valves, each requiring attention, are simultaneously operative.

The maintenance of normal pressure within an eye during surgical procedures is important for a number of reasons. A constant pressure, at a natural level, tends to preserve and stabilize the spatial relationships of the intra-ocular tissues. These spacial relationships are important in order to maintain the optical parameters of the lens and eye. Variation of pressure during the operation may detract from the surgeon's ability to focus on intra-ocular tissues. Excess pressure, as known in connection with glaucoma, restricts blood circulation to eye tissues, causing damage. Nerve cells lost, for example due to oxygen starvation caused by lack of circulation, cannot be recovered. Overpressure closes off circulation through the capillaries. Variation in pressure, and also excess volume of flow through the eye, can result in loss of endothelial cells. These cells generate a natural fluid flow to the cornea, and their loss can be a cause of clouding in the long run. Another consideration is the statistical increase in probability of infection which must result from introduction of an increased volume of foreign fluid.

Conventional teachings in the art regarding pressure control have not kept pace with the sophisticated incision and emulsification apparatus known in the art. Excess flow is ignored and only pressure is controlled. Instead of instruments which are both precise and highly dependable, the art teaches pressure and flow control apparatus which although probably precise are highly complicated.

Aside from the relatively delicate apparatus and special needs of opthalmic surgery, devices are available for more or less simultaneously exchanging a body fluid with a fluid held in an external container. U.S. Pat. No. 4,112,947-Nehring teaches a combined irrigator and evacuator for closed wounds. A single housing defines a space divided into two sections by a movable divider. The divider may be spring biased or mounted on a resilient membrane which biases the device, providing pressure to empty a reservoir into the wound, and to extract a quantity of fluid from the wound. Various stopcocks, check valves and access points are provided for initially biasing the device, or for maintaining required conditions.

U.S. Pat. No. 3,411,502-Hofstra, et al., teaches sequentially infusing and aspirating small volumes of fluid, for example, to quickly accomplish a blood transfusion in newborns having Rh difficulties. Simultaneously operated expansible chambers are connected in a "Y," and valved such that one of the chambers discharges forward and draws fluid from rearward, and the other chamber operates oppositely. Both chambers have associated reservoirs and each requires at least one one-way valve. By pumping the paired chambers, an overall effect of moving fluid from a first reservoir to a body cavity, and from the cavity into a second reservoir, is accomplished. Of course, such an apparatus will result in a periodic variation in flow rate and pressure, due to the pumping of the paired expansible chambers. Therefore, the apparatus is not believed to be useful for intra-ocular manipulations.

According to the invention, intra-ocular pressure is maintained at its normal value, and aspiration of emulsified tissue may proceed, without requiring a large steady-state flow of fluid, as required in the saline column/drain apparatus. Sufficient fluid to accomplish the aspiration of cortical material and/or emulsified cataract material and the replacement of the aspirated material with an infusion is supplied; however, this is not done by depending upon an asymmetrically-powered flow through an open drain tube. Moreover, separately controlled or separately operable pressure and suction supplies are avoided. Any obstruction or disturbance in the supply or in the exhaust will not develop into an imbalance in the pressure of fluid supplied, because supply and removal of fluid are positively linked.

According to the invention, expansible supply and exhaust chambers are directly linked to one another, and the linked system is driven in a closed loop. Should any obstruction occur, for example, in the supply side, the linkage of the supply and drain mechanisms will cause both to cease operation, thereby absolutely preventing deflation, over-inflation or other pressure variation in the eye. The device may comprise piston and cylinder assemblies, such as syringes, or other expansible bodies, directly and mechanically linked. In normal operation the mechanical linkage absolutely precludes any variation between the rates of supply and discharge of fluid, which rates would otherwise require individual attention and balancing. The device can be embodied in a series of attachments, and may also be adapted for use together with an incision, aspiration and infusion tool, for example, having a series of concentric passageways.

SUMMARY OF THE INVENTION

It is an object of the invention to normalize intra-ocular pressure in a device for endophthalmic surgery with maximum dependability and minimum expense.

It is another object of the invention to allow aspiration and infusion of a body cavity to be simultaneously carried out without a possibility of pressure imbalance.

It is also an object of the invention to adapt the syringes and hypodermic needles conventional to ophthalmic surgery to a device operable to control intra-ocular pressure.

It is yet another object of the invention to mechanically link an aspiration mechanism and an infusion mechanism, in order to positively control pressure in a body cavity being simultaneously aspirated and infused.

These and other objects are accomplished by an apparatus for maintaining pressure in a body cavity while simultaneously removing and replacing fluid therein, the apparatus comprising at least two expansible bodies such as syringes having barrels and movable plungers therein, each syringe being adapted for fluid connection to the body cavity; and, means for equally and oppositely displacing the plungers in the barrels. As specifically adapted for controlling intra-ocular pressure during eye surgery, the apparatus comprises first and second hollow needles for insertion through a surface of the eye; first and second expansible bodies of equal size having portions movable therein to effect expansion and contraction of fluid reservoirs defined by the expansible bodies, one of the bodies adapted to discharge a fluid and the other adapted to draw in a fluid; conduits connecting the hollow needles to the reservoirs of the expansible bodies; and, drive means operable to displace the movable portions of the expansible bodies in register and in opposite directions, whereby equal volumes of fluid are drawn in and discharged to the eye. Paired hypodermic needle barrels may be rigidly mounted with respect to one another, and a linkage connected between the plungers and/or barrels thereof. The barrels and plungers are preferably mounted parallel to one another, for example along the same axis. Relative movement between attached plungers and attached barrels effects equal and opposite operation of the syringes, and simultaneous infusion and aspiration at precisely equal volumes.

BRIEF DESCRIPTION OF THE DRAWINGS

There are shown in the drawings the embodiments which are presently preferred. It should be understood, however, that the invention is not limited to the precise arrangements and instrumentalities shown in the drawings, wherein.

DETAILED DESCRIPTION OF THE PREFERRED EMBODIMENTS

According to the invention, a pair of expansible bodies may be aligned for operation in opposite directions, and mechanically attached to one another. Any expansion of a first attached body causes an equal contraction of the second body. In connection with intra-ocular surgery, an arrangement employing syringes having tubular barrels and plungers axially movable therein may be attached according to this description in order to simultaneously aspirate cprtoca; ,ateroa; and/or emulsified cataract material, and to infuse a precisely equal volume of a balanced salt solution.

Figure 1:
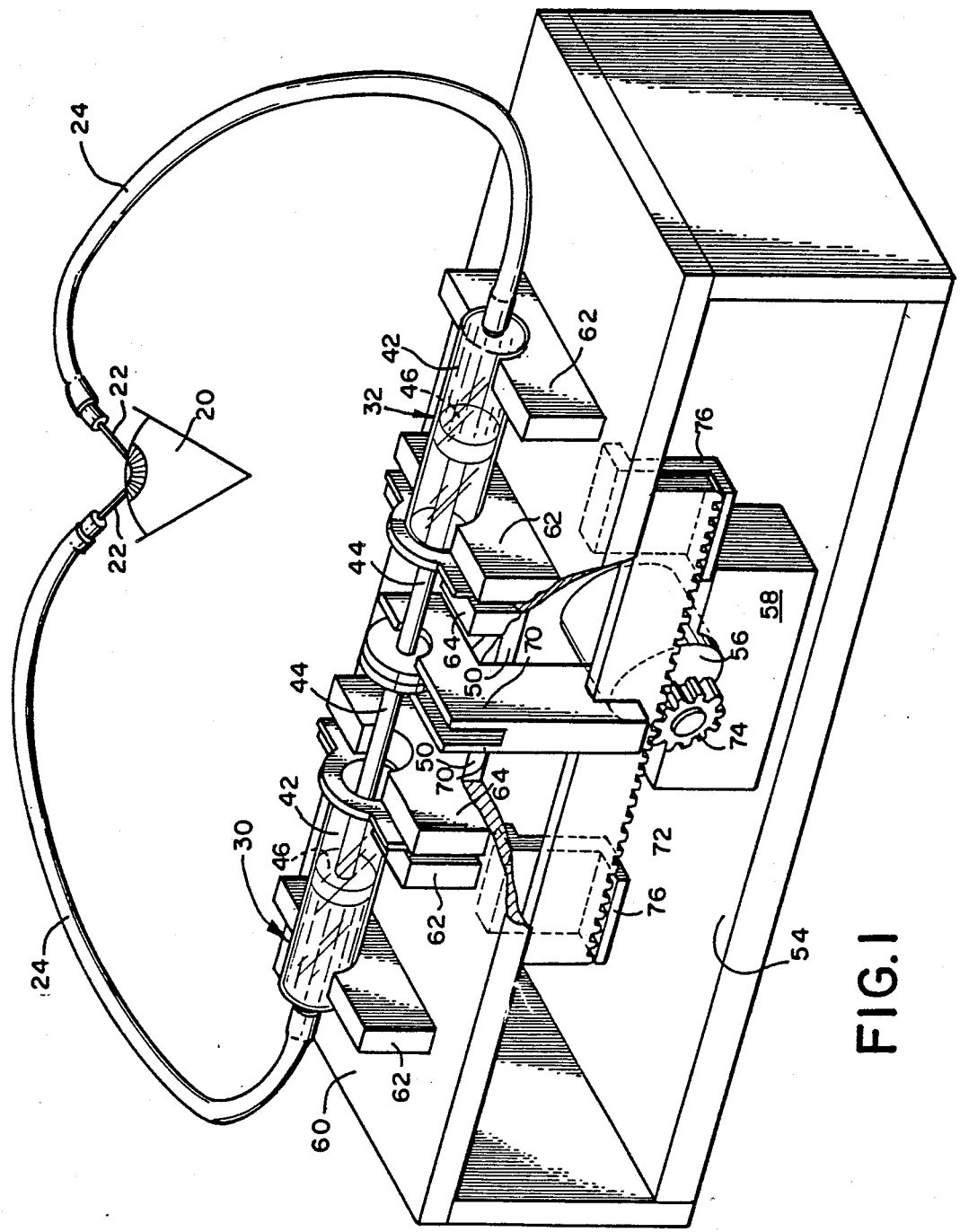
FIG. 1 is a cut-away perspective view of an apparatus according to the invention.

A preferred embodiment of the invention is shown in FIG. 1. A pair of syringes 30, 32 are attached via conduits 24 to hypodermic needles 22. The hypodermic needles are inserted at the edges of the cornea of eye 20, into the anterior aqueous chamber immediately adjacent the lens. This procedure may also be employed for manipulations of the vitreous membranes, that is, the jelly-like membrane behind the lens, or for that matter in any body cavity for which syringes 30, 32, conduits 24 and needles 22 are appropriately dimensioned. It is nevertheless believed that the device is particularly suited for endophthalmic surgery due to the precise metering which results from the mechanical connection of equally dimensioned collapsible reservoirs, that is, syringes 30, 32.

Each syringe 30, 32 comprises a barrel 42, a plunger 44, axially movable within the barrel, the plunger operable to move a cylindrical seal 46 axially within the hollow of barrel 42. The volume defined by the seal 46 and barrel 42 is altered in proportion to the displacement of a seal 46 along the axis of the barrel.

Syringes 30, 32 may be conventional disposable plastic syringes. However, the hypodermic needles normally associated with the syringes, for example, needles 22, have been removed from the discharge end of the syringes and connected thereto by means of conduits 24. The volumes required for syringes 30, 32, as well as the inner diameter of conduits 24 and needles 22, will depend upon the particular flow requirements of a given situation. For example, it is presently preferred that 10 cc. syringes be employed with conduits and needles having inner diameters of approximately 0.3 mm. (0.010 in.) in order to conduct a five to ten minute intra-ocular procedure on the anterior aqueous chamber, which has a volume of approximately one cc. The rate of flow is preferably adjustable as required to accommodate the needs of various operations such as cataract removal.

The arrangement according to the invention is preferably mounted in a box 54, having a cover table 60, upon which the syringes 30, 32 are mountable, and an enclosed portion for housing a motor 56. The syringe barrels are connected and the syringe plungers are connected, relative movement between the plungers and the barrels causing equal and opposite syringe operation. The plungers 44, 44 of the syringes 30, 32 may be rigidly attached endwise to one another by means of plunger clip 68. Clip 68 has a pair of spaced plates 70 defining U-shaped clamp members for engaging the ends of plungers 44. Plungers 44, as is conventional, comprise an enlarged disk at the end of a shaft. The U-shaped clamps engage the plungers just behind the disks. The disks fit tightly into clip 68, holding the plungers fast with respect to one another.

The plunger clip 68 is carried on a standing member 66, which extends through a slot 50 in table 60. The standing member 66 is attached below the surface of table 60, to a drive mechanism operable to linearly displace clip 68, and to thereby move both plungers 44, over a span along an axis defined by the oppositely facing syringes 30, 32 and their plungers.

On the surface of table 60, means are provided for rigidly holding the barrels of syringes 30, 32 against axial movement with respect to one another. In particular, syringes 30, 32 are mounted in cradle members 62, having channels formed therein along the common axis. An additional block 64 is preferably provided to engage behind the usual flanged end of the barrel 42. Upon insertion of barrel 42 into the receptacle defined by cradle members 62 and blocks 64, barrel 42 is held rigidly along its axis and maintained at the same axial orientation on table 60 as the other barrel 42.

Located immediately below table 60, toothed rail or rack 72 is rigidly attached to the standing member 66 terminating in the plunger clip 68 above table 60. Rack 72, which may be considered a linear gear, is driven along the axis by pinion gear 74, mounted on the shaft of gearmotor 56. Motor 56 is mounted inside box 54 by means of motor mount 58, whereby the drive mechanism is rigidly attached to box 54. Accordingly, the barrels and drive means are rigidly attached to the box, and the only movable elements are the plungers and the driven rack and plunger-engaging mechanism. The plunger-engaging mechanism, including clip 68, stand 66, and gear 72, moves back and forth with respect to coverplate 60 and box 54, rack 72 being slidably carried by slides 76 or the like.

In order to conduct simultaneous aspiration and infusion, one of the two syringes 30, 32 is initially filled, for example, with a balanced salt solution or normal saline solution, and the other syringe is initially empty or nearly empty. The initially empty syringe may be connected to the needle which is closer to the cataract material to be removed, the other needle being placed anywhere in fluid communication with the anterior aqueous chamber of eye 20. Motor 56 is preferably a gear motor with a substantial step-down gear train. The precise rate of movement may vary over a predetermined range of flow-rate control. Depending on the control, the motor and the load, a gear reduction, for example, of three thousand to one results in linear displacement of plungers 44 of approximately one-half inch per minute, allowing the surgeon five to ten minutes to complete the breakdown and aspiration of emulsified cataract material, before any change of syringes is required. This period is normally sufficient to complete the procedure without changing the syringes. In any event, changing the syringes is easy and convenient in that motor 56 is preferably reversible, whereby, upon exhausting the capacity of a first fluid load, the box may be reversed and a new supply of solution and a new empty syringe inserted. It is not recommended that the direction of the conduits be reversed, as any emulsified cataract material remaining in the conduits could be discharged into the aqueous chamber of the eye.

A variable-speed motor may be advantageously used to control flow rate, as opposed to control using a load-varying element such as a needle valve or the like. It should be appreciated that the mechanical linkage of elements causes the supply and discharge rates to remain equal even if one of the conduits is partially obstructed. Therefore, an adjustable obstruction may be used in either conduit to control the rate of flow throughout the system. Restriction of flow in this manner is somewhat a strain on the motor and makes rate adjustment rather a matter of guesswork. Accordingly, a variable speed motor is the preferred means of altering flow rate. A variable speed motor arrangement appropriate to the invention may include a motor and a variable power supply, the variable power supply having a control marked or otherwise correlated to flow rates. For example, a DC motor may be used with a variable DC power supply. As another alternative, a stepping motor can be used together with a pulse train generator having means to adjust the rate of pulse production. Either of these alternatives may be used to the end of supplying a rate of flow variable around the optimum rate for a given operation. A variation, for example, of 50% around optimum allows a good range of adjustment for particular circumstances. Another possible variation is reversible drive operable to change directions. The reverse may also drive the system at a much higher rate in reverse than in forward, in order to quickly return to a starting position.

Figure 2:
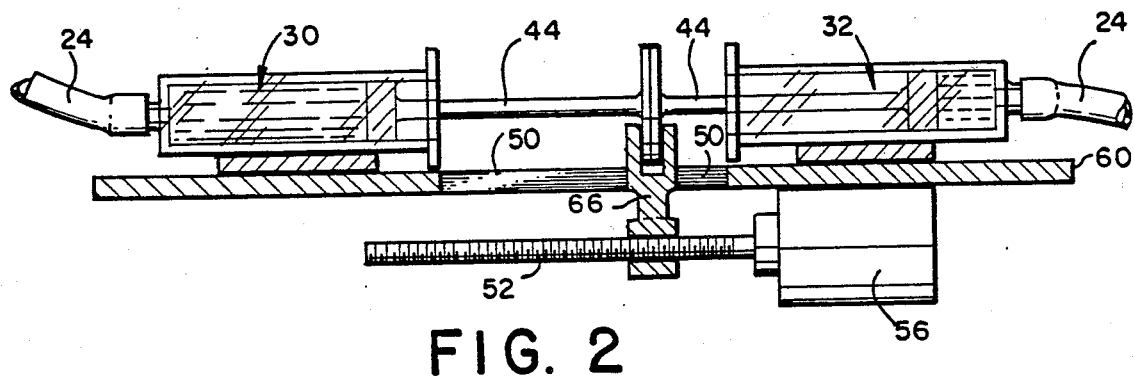
FIG. 2 is a partial section view of the apparatus according to FIG. 1, showing an alternate drive means.
Figure 3:
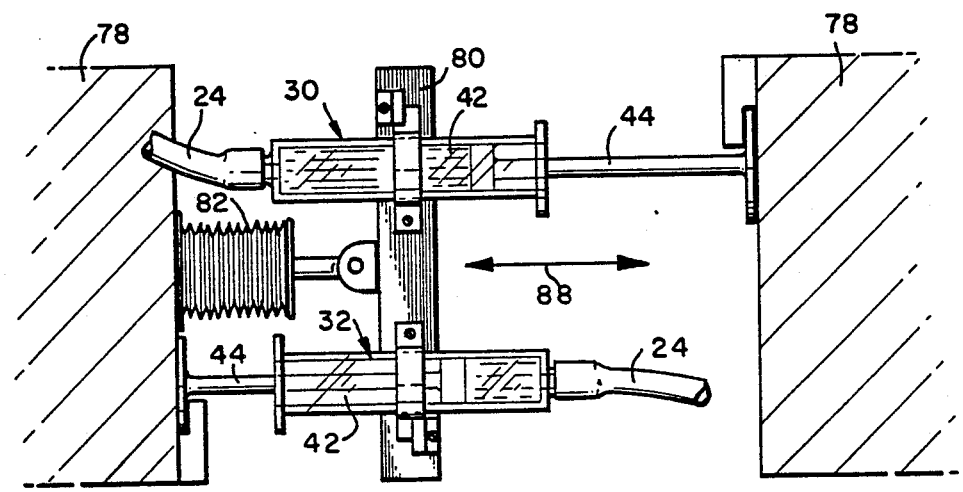
FIG. 3 is an elevation view of an alternative embodiment according to the invention.
Figure 4:
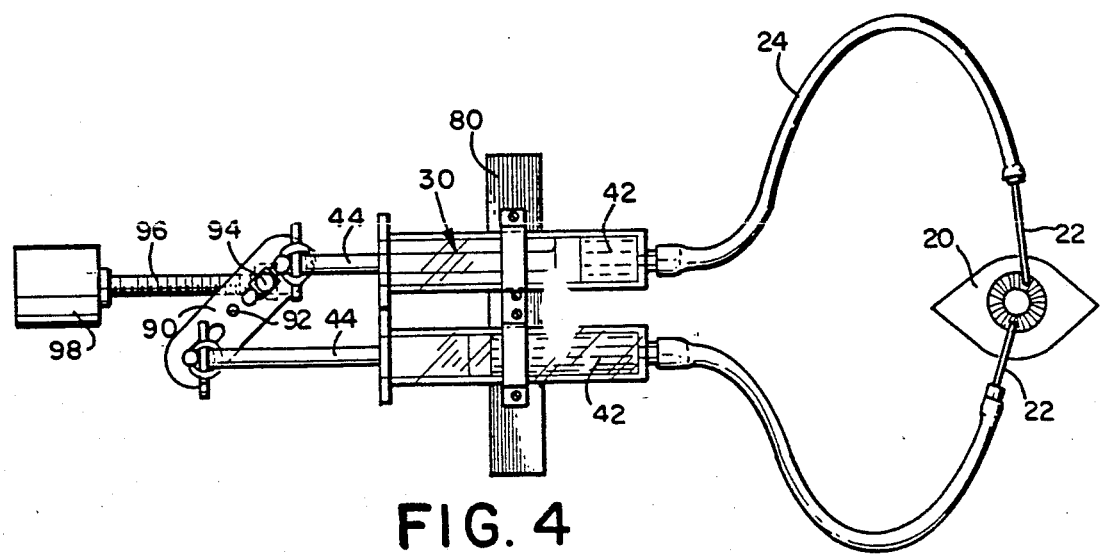
FIG. 4 is an elevation view of yet another alternative embodiment of the invention.

Additional embodiments of the invention are illustrated in FIGS. 2 through 4. The basic requirement is only that means be provided to ensure that the displacement of the expansible bodies is exactly equal, whereby the supply volume is necessarily exactly equal to the discharge volume and no pressure variation is possible. This may be accomplished by holding the barrels and moving the plungers, or vice-versa. Moreover, various attachments by which one or the other of the plungers and the barrels may be held and/or moved are possible.

In FIG. 1, a linear movement is driven by a variable speed reduction motor 56, pinion gear 74 and rack 72. With reference to FIG. 2, a linear movement may likewise be arranged using a threadable connection between the shaft of motor 56 and the standing member 66, adapted to engage the plungers at clip 66. Clip 66, as in the previous embodiment, is linearly displaceable along the axis defined by the barrels of syringes 30, 32, within a space defined by alot 50 in table 60. Inasmuch as a relatively fine threadable connection is possible between threaded shaft 52 and standing member 66, a gear reduction substantially less that that required for a rack/pinion arrangement will suffice in gear motor 56, without sacrificing the span of displacement. Alternatively, the speed control can be based only on a timing mechanism and a stepping motor, precluding the need for step-down gears. The remaining details in mounting of the syringe barrels, and in the box enclosing the gear motor and the like, are shown in FIG. 1. It will be appreciated that motor 56 may be mounted directly to the underside of table 60, and various alternatives may be undertaken for supporting table 60, and for attaching syringes 30, 32 rigidly with respect to one another.

As shown in FIG. 3, a fluid-driven pneumatic or hydraulic linkage is also possible. Expandable cylinder 82, which may be pneumatic or hydraulic, drives the two barrels 42 in a direction parallel to their axes, that is, the direction indicated in FIG. 3 by the double arrow 88. Barrels 42 are affixed to movable portion 80 by means of spring clips or the like. In any event, barrels 42 are rigidly attached with respect to one another, and movable along their axes. It will be appreciated that unlike the previous embodiments, the embodiment of FIG. 3 does not require that the syringes be mounted along a common axis, but only that a linkage is provided to inevitably displace the plungers 44 with respect to barrels 42 by exactly equal and opposite amounts. Plungers 42 are rigidly attached to sidewalls 78, which are immovable with respect to one another. For example, sidewalls 78 may be portions of a single integral member or rigidly built cabinet or table member, similar to table member 60 of the embodiment of FIG. 1. As before, conduit members 24 in FIG. 3 are to be connected to hypodermic needles 22, inserted through the surface of eye 20, for example into the anterior aqueous chamber (see FIG. 1).

The connection between the plungers 44, or barrels 42, need not be the absolutely rigid and linearly movable arrangements shown in FIGS. 1-3. As shown in FIG. 4, a pivotable connection will also positively and mechanically link the motion of the two plungers 44, or two barrels 42, the other of the pairs being rigidly held. In FIG. 4, a pivoting linkage bar 90, adapted to pivot around pivot pin 92, is resiliently connected to the end of each plunger 44. A threaded nut 94, slidable within a slot on arm 90, is engaged by threaded shaft 96 of motor 98, whereby substantially linear movement of nut 94 along threaded shaft 96 is converted into opposite linear movements of the two plungers 44 within barrels 42, mounted to carrier 88. In order to provide a smooth movement of the linkage of FIG. 4, it is necessary to also slot the connection between arm 90 and the plungers, and/or to allow angular displacement of nut 94 and plungers 44 with respect to pivot arm 90. At least for plastic syringes, the shafts 44 of the plungers are relatively resilient and easily displaced from their axes. If plungers 44 are mounted to slide along slots in arm 90, the plungers 44 will move only axially. Alternatively, the barrels can be mounted to pivot sufficiently, for example around their discharge end, to keep the barrels and plungers aligned as arm 90 pivots.

According to the present invention, simultaneous aspiration and infusion can be conducted for as long as necessary, and in appropriate volumes, for the procedure undertaken. The invention is especially useful to emulsify and aspirate the clouded or opaque portion of a lens, while infusing a precisely equal amount of balanced salt solution or the like. The flow-regulating apparatus according to the invention can be suitable combined with a hand-held incision and/or emulsifying tool, or employed concurrently with such an apparatus. The overall quantity of fluid which is required to be washed through the intra-ocular chamber is minimized, and the pressure therein precisely maintained. Should one of the conduits 24 become obstructed, any pressure or suction build-up will occur between the obstruction and the respective syringe, and not in the eye. Moreover, such a pressure or suction build-up will be mechanically transmitted to the other of the syringes, also stopping movement therein.

A major benefit of the invention is mechanically linking the infusion and aspiration mechanisms such that precisely equal volumes are supplied and removed, resulting in a zero pressure change in eye 20. It will be appreciated that a pressure differential or gradient necessarily exists in order to cause a flow of infused or aspirated material. So long as plungers 44 are in motion with respect to barrels 42, at least a small pressure differential will exist, and flow will proceed. Upon stopping motion of the plungers, pressures will promptly equalize and flow will stop. Therefore, the precise pressure differential in the eye and in the apparatus will depend on the rate of motion of the plungers, as well as the characteristic resistance of flow through conduits 24 and needles 22. Such characteristic resistance is primarily a function of the internal diameter of conduits 24 and needles 22. Inasmuch as the cross-section of the conduits and needles is much smaller than the cross-section of the anterior aqueous chamber, the pressure differential occurs primarily in the conduits and needles. By using equal lengths of conduit at the supply and discharge sides, the eye can be located at a neutral point between the pressure supply and suction discharge syringes.

Specific pressure differentials, flow rates and volumes are subject to variation as needed for the particular operation in progress. For infusion/aspiration of a relatively larger body cavity, larger syringes and larger conduits are appropriate, thereby accommodating a given rate of flow and a given number of fluid changes per unit of time. In connection with intra-ocular surgery, where precise pressure control is important, it is presently preferred that 5–10 cc's of fluid be provided for exchange over a treatment period ranging from five to ten minutes. The components of the invention are therefore chosen to supply a flow rate of approximately 1 cc. per minute which, together with conduits and hypodermic needles having an internal diameter of approximately 0.3 mm., provides acceptable results. Persons skilled in the art will nevertheless appreciate that the specific values of dimensions and flow will vary widely, for example, for procedures needing greater flow or affecting fluids of different characteristics, such as that of the vitreous chamber of the eye, or other body cavities.

The device of the invention may be advantageously used with an incising or emulsifying tool having internal conduits for aspiration and/or infusion. In that event, the "needles" are, in fact, internal conduits in the tool, for example, coaxial passages. The invention is subject to many variations, for example syringes having barrels of unequal dimensions may be employed for the supply and withdrawal sides of the apparatus. In this event, a linkage causing a corresponding proportionate displacement will be required to maintain equal rates of flow. Alternatively, an unequal rate of flow may also be deliberately employed in order to offset a known degree of incidental leakage of fluid from the body cavity, for example, around the point of insertion of the needles.

A further variation employs permanently-fused plungers, the two syringe barrels being oppositely disposed on a single plunger body having a seal on each end. The unitary plunger body is then anchored and the barrels moved; or alternatively, the barrels can be anchored and the plunger body displaced. It is also possible to operate a plurality of syringes for infusion and a corresponding plurality for aspiration.

The invention having been disclosed, a number of additional variations will now occur to persons skilled in the art. Reference should be made to the appended claims rather than the foregoing specification as indicating the true scope of the invention.

What is claimed is:

1. An apparatus for controlling intra-ocular pressure during eye surgery wherein material is to be removed from an eye, the apparatus comprising:
   first and second hollow tube means for insertion through a surface of the eye, the first and second hollow tube means defining an internal diameter of about 0.3 mm (0.010 in.);
   first and second expansible bodies of equal size, the expansible bodies each having a maximum capacity in the range of about 5–10 cc's, said bodies having portions movable therein to effect expansion and contraction of fluid reservoirs defined by the bodies, one of the bodies being connected in unobstructed fluid communication with said tube means to discharge a fluid and the other of the bodies being connected in unobstructed fluid communication with said tube means to draw in a fluid;
   conduits connecting the hollow tube means to the reservoirs of the expansible bodies to form, in conjunction with said tube means and said expansible bodies a substantially closed and unobstructed fluid system leading from one of the bodies through the eye to the other of the bodies; and,
   drive means operable to displace the movable portions of the expansible bodies in register and in opposite direction, whereby equal volumes of fluid are drawn in and discharged to the eye substantially isometrically and isobarically with respect to said eye.

2. The apparatus of claim 1, wherein the hollow tube means include hypodermic needles and the expansible bodies are syringes wherein said movable portions are hollow barrels carrying axially-movable plungers.

3. The apparatus of claim 2, further comprising first mounting means rigidly attached to the barrels and second mounting means rigidly attached to the plungers, the barrels and plungers being positioned parallel and oppositely oriented,, the drive means operable to displace the first and second mounting means, relative to one another.

4. The apparatus of claim 3, wherein the syringes are oppositely oriented along an axis, and the plungers are endwise attached to one another, the barrels being spaced by a distance substantially equal to a span of axial travel of one of the plungers.

5. The apparatus of claim 4, wherein the drive means is mounted to the first mounting means and the drive means includes a motor means for linear displacement, attached to an end of the plungers, along the axis.

6. The apparatus of claim 5, wherein the first mounting means comprises a table and the second mounting means comprises a clamp member, the clamp member having a portion engaged by a shaft driven by the motor.

7. The apparatus of claim 6, wherein the engaged portion and the driven shaft comprise interfitting gears.

8. The apparatus of claim 6, wherein the engaged portion and the driven shaft comprise interfitting threads.

9. The apparatus of claim 4, wherein the drive means comprises an expansible cylinder.

10. The apparatus of claim 1, wherein the expansible bodies are syringes having hollow barrels, the syringes being oppositely oriented, fixed along an axis, and facing in opposite directions and having a controllably movable plunger body disposed therein, displacement of the plunger body expanding one of the reservoirs and contracting the other of the reservoirs.

11. An apparatus for simultaneously drawing and discharging equal amounts of fluid from an eye cavity, comprising:
   two barrels, each defining a reservoir having a full volume of about 5–10 cc's and having an outlet passage at an end of said reservoir, the outlet passages for the two barrels being disposed at opposite ends of said barrels and being fluidly coupleable, via respective means for connecting, to an eye cavity and forming a substantially closed and unobstructed fluid system; and, a plunger body having means on opposite ends thereof dimensioned to movably seal the plunger body to portions of the barrels said defining reservoirs to thereby vary a volume of the reservoirs between zero and said full volume, whereby upon fixing the barrels and moving the plunger body, one of the reservoirs takes in and the other of the reservoirs discharges, through the respective outlet passages for said reservoirs, a predetermined equal amount of the fluid moving from and into said eye cavity substantially isometrically and isobarically with respect to said eye cavity.

12. The apparatus of claim 11, wherein the barrels are syringe barrels axially aligned and oppositely oriented, and the plunger body is a double ended syringe plunger.

* * * * *

UNITED STATES PATENT AND TRADEMARK OFFICE
CERTIFICATE OF CORRECTION

PATENT NO. : 4,909,783
DATED : March 20, 1990
INVENTOR(S) : Morrison

It is certified that error appears in the above-identified patent and that said Letters Patent is hereby corrected as shown below:

Column 5, line 12, delete "cprtoca; , ateroa;" and insert --cortical material--.

Column 7, line 41, delete "alot" and insert --slot--.

Column 12, line 9, delete "fhe" and insert --the--.

Signed and Sealed this

Eighteenth Day of June, 1991

Attest:

HARRY F. MANBECK, JR.

Attesting Officer

Commissioner of Patents and Trademarks